United States Patent
Belcher et al.

(10) Patent No.: US 11,976,270 B2
(45) Date of Patent: May 7, 2024

(54) OPTIMIZATION OF CIRCULAR SINGLE STRANDED DNA USING M13 PHAGE

(71) Applicant: Massachusetts Institute of Technology, Cambridge, MA (US)

(72) Inventors: Angela Belcher, Lexington, MA (US); Christopher A. Voigt, Belmont, MA (US); Uyanga Tsedev, Somerville, MA (US); Tae-Gon Cha, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 106 days.

(21) Appl. No.: 16/874,480

(22) Filed: May 14, 2020

(65) Prior Publication Data

US 2020/0362332 A1    Nov. 19, 2020

Related U.S. Application Data

(60) Provisional application No. 62/848,449, filed on May 15, 2019.

(51) Int. Cl.
 C12N 15/70    (2006.01)
 C12N 15/10    (2006.01)

(52) U.S. Cl.
 CPC ......... *C12N 15/1003* (2013.01); *C12N 15/70* (2013.01); *C12N 2310/532* (2013.01)

(58) Field of Classification Search
 None
 See application file for complete search history.

(56) References Cited

U.S. PATENT DOCUMENTS 10,987,388 B2    4/2021   Belcher et al.
2007/0219361 A1  9/2007   Bodepudi et al.

FOREIGN PATENT DOCUMENTS

AU    2008200988 A1    3/2008
WO    WO 2002/006860 A1    9/2002
WO    WO 2019/044820 A1    3/2019

OTHER PUBLICATIONS

Nomura and Ray, GenBank Accession No. M10568.1, Apr. 1993.*
Horiuchi, Genes to Cells, vol. 2, pp. 425-432, 1997.*
Nafsi et al., GenEmbl database Accession No. MH319458, Jul. 17, 2018.*
International Search Report and Written Opinion for PCT/US2020/032960 dated Jul. 20, 2020.
International Preliminary Report on Patentabilit for PCT/US2020/032960 dated Nov. 25, 2021.
Nafisi, Improving the production of highly custom single-stranded DNA sequences for applications in DNA nanotechnology through the development of novel bacteriophage-based DNA-production methods. University of California. 2018.
Nafisi et al., Construction of a novel phagemid to produce custom DNA origami scaffolds. Synth Biol (Oxf). Jan. 2018;3(1):ysy015. doi: 10.1093/synbio/ysy015. Epub Aug. 9, 2018. PMID: 30984875; PMCID: PMC6461039.
PCT/US2020/032960, Jul. 20, 2020, International Search Report for Written Opinion.
PCT/US2020/032960, Nov. 25, 2021, International Preliminary Report on Patentability.
Benzinger et al., Infectious nucleic acids of *Escherichia coli* bacteriophages. 10. Preparation and properties of *Escherichia coli* competent for infectious DNA from bacteriophages phi X 174 and M 13 and RNA from bacteriophage M 12. Eur J Biochem. Nov. 1967;2(4):414-28.
Chen et al., High-frequency genome editing using ssDNA oligonucleotides with zinc-finger nucleases. Nature Methods 8, 753-755, doi:10.1038/nmeth.1653 (2011).
Cong et al., Multiplex genome engineering using CRISPR/Cas systems. Science. Feb. 15, 2013;339(6121):819-23. doi: 10.1126/science.1231143. Epub Jan. 3, 2013.
Dotto et al., Initiation and termination of phage f1 plus-strand synthesis. Proc Natl Acad Sci U S A. Dec. 1982;79(23):7122-6.
Ducani et al., Enzymatic production of 'monoclonal stoichiometric' single-stranded DNA oligonucleotides. Nat Methods. Jul. 2013;10(7):647-52. doi: 10.1038/nmeth.2503. Epub Jun. 2, 2013.
Gyllensten et al., Generation of single-stranded DNA by the polymerase chain reaction and its application to direct sequencing of the HLA-DQA locus. Proc Natl Acad Sci U S A. Oct. 1988;85(20):7652-6.
Han et al., Single-stranded DNA and RNA origami. Science. Dec. 15, 2017;358(6369):eaao2648.
Hultman et al., Direct solid phase sequencing of genomic and plasmid DNA using magnetic beads as solid support. Nucleic Acids Res. Jul. 11, 1989;17(13):4937-46.
Kosuri et al., Large-scale de novo DNA synthesis: technologies and applications. Nat Methods. May 2014;11(5):499-507.
Pires et al., Genetically Engineered Phages: a Review of Advances over the Last Decade. Microbiol Mol Biol Rev. Jun. 1, 2016;80(3):523-43.
Pope et al., Cluster K mycobacteriophages: insights into the evolutionary origins of mycobacteriophage TM4. PLoS One. 2011;6(10):e26750. doi: 10.1371/journal.pone.0026750. Epub Oct. 28, 2011.
Rothemund. Folding DNA to create nanoscale shapes and patterns. Nature. Mar. 16, 2006;440(7082):297-302.
Sorokin et al., A new approach using multiplex long accurate PCR and yeast artificial chromosomes for bacterial chromosome mapping and sequencing. Genome Res. May 1996;6(5):448-53.
Tsedev, Engineering M13 bacteriophage platforms for cancer therapy applications. Thesis. Jun. 2015: 48 pages.

* cited by examiner

*Primary Examiner* — Richard G Hutson
(74) *Attorney, Agent, or Firm* — Wolf, Greenfield & Sacks, P.C.

(57)    ABSTRACT

Provided herein, in some aspects, are methods and compositions for producing single-stranded DNA (ssDNA) having uniform length.

8 Claims, 6 Drawing Sheets

Specification includes a Sequence Listing.

OPTIMIZATION OF CIRCULAR SINGLE STRANDED DNA USING M13 PHAGE

RELATED APPLICATIONS

This application claims priority under 35 U.S.C. § 119(e) to U.S. Provisional Application No. 62/848,449, filed May 15, 2019 and entitled "Optimization of Circular Single Stranded DNA Using M13 Phage," which is incorporated herein by reference in its entirety for all purposes.

GOVERNMENT SUPPORT

This invention was made with Government support under Grant No. HR0011-15-C-0084 awarded by the Defense Advanced Research Projects Agency (DARPA). The Government has certain rights in the invention.

BACKGROUND OF THE INVENTION

Single-stranded DNA (ssDNA) may be used in a variety of biotechnology applications including genome editing, gene synthesis, gene therapy, and drug delivery. Conventional approaches produce ssDNA having various lengths, which is then purified to obtain ssDNA of a monodisperse length. Accordingly, methods that produce ssDNA having uniform length may eliminate the need for labor-intensive and expensive purification steps.

SUMMARY OF THE INVENTION

Provided herein are compositions and methods for producing single-stranded DNA (ssDNA) having uniform length that are rapid and cost-effective. Producing ssDNA of a uniform length, in some embodiments, is achieved using an engineered initiator sequence and an engineered terminator sequence from a filamentous bacteriophage.

Accordingly, one aspect of the present disclosure provides an engineered nucleic acid comprising an engineered initiator sequence and an engineered terminator sequence from a filamentous bacteriophage; and a DNA sequence of interest, wherein the DNA sequence of interest is located 3' to the engineered initiator sequence and 5' to the engineered terminator sequence.

In some embodiments, the engineered nucleic acid further comprises a selectable marker. In some embodiments, the engineered nucleic acid is single stranded. In some embodiments, the engineered nucleic acid is double stranded. In some embodiments, the engineered nucleic acid is linear. In some embodiments, the engineered nucleic acid is circular. In some embodiments, the engineered nucleic acid is circular and double stranded.

In some embodiments, the engineered initiator sequence comprises a nucleic acid sequence having at least 80% identity to SEQ ID NO: 1. In some embodiments the engineered initiator sequence comprises a nucleic acid sequence having at least 80% identity to SEQ ID NO: 2. In some embodiments the engineered initiator sequence comprises a nucleic acid sequence having at least 85%, 90%, 91%, 92%, 93%, 94%, 95%, 96%, 97%, 98%, or 99% identity to SEQ ID NO: 2. In some embodiments, the engineered initiator sequence comprises SEQ ID NO: 2. In some embodiments, the engineered terminator sequence comprises a nucleic acid sequence having at least 80% identity to SEQ ID NO: 1. In some embodiments, the engineered terminator sequence comprises SEQ ID NO: 3. In some embodiments the engineered terminator sequence comprises a nucleic acid sequence having at least 85%, 90%, 91%, 92%, 93%, 94%, 95%, 96%, 97%, 98%, or 99% identity to SEQ ID NO: 3.

In some embodiments, the DNA sequence of interest is between 100 and 20,000 nucleotides in length.

Aspects of the present disclosure provide, in some embodiments, a host cell comprising (a) an engineered nucleic acid comprising an engineered initiator sequence and an engineered terminator sequence from a filamentous bacteriophage; and a DNA sequence of interest, wherein the DNA sequence of interest is located 3' to the engineered initiator sequence and 5' to the engineered terminator sequence, and (b) a nucleic acid helper plasmid for expressing a plurality of bacteriophage proteins capable of assembling a single-stranded DNA (ssDNA) into a bacteriophage.

In some embodiments, the host cell is a bacterial cell. In some embodiments, the bacterial cell is an *E. coli* cell. In some embodiments, the plurality of bacteriophage proteins comprises P1, P2, P3, P4, P5, P6, P7, P8, P9, P10, and P11.

Aspects of the present disclosure provide, in some embodiments, a method for producing single-stranded DNA (ssDNA) having uniform length comprising (a) culturing a host cell provided herein under conditions suitable for producing a ssDNA from the DNA sequence of interest in the engineered nucleic acid and the plurality of bacteriophage proteins from the nucleic acid helper plasmid; (b) allowing the ssDNA and the plurality of bacteriophage proteins to assemble into an engineered phage; and (c) collecting the engineered phage.

In some embodiments, methods provided herein further comprise extracting the ssDNA from the engineered phage. In some embodiments, at least 90% of the ssDNA is the same length as the DNA sequence of interest. In some embodiments, at least 95% of the ssDNA is the same length as the DNA sequence of interest. In some embodiments, the ssDNA is between 100 and 20,000 nucleotides in length. In some embodiments, the ssDNA is circular.

The details of several embodiments of the invention are set forth in the accompanying Examples, Figures and the Detailed Description. Other features, objects, and advantages of the invention will be apparent from the description and from the claims.

DETAILED DESCRIPTION OF THE INVENTION

Figure 1:
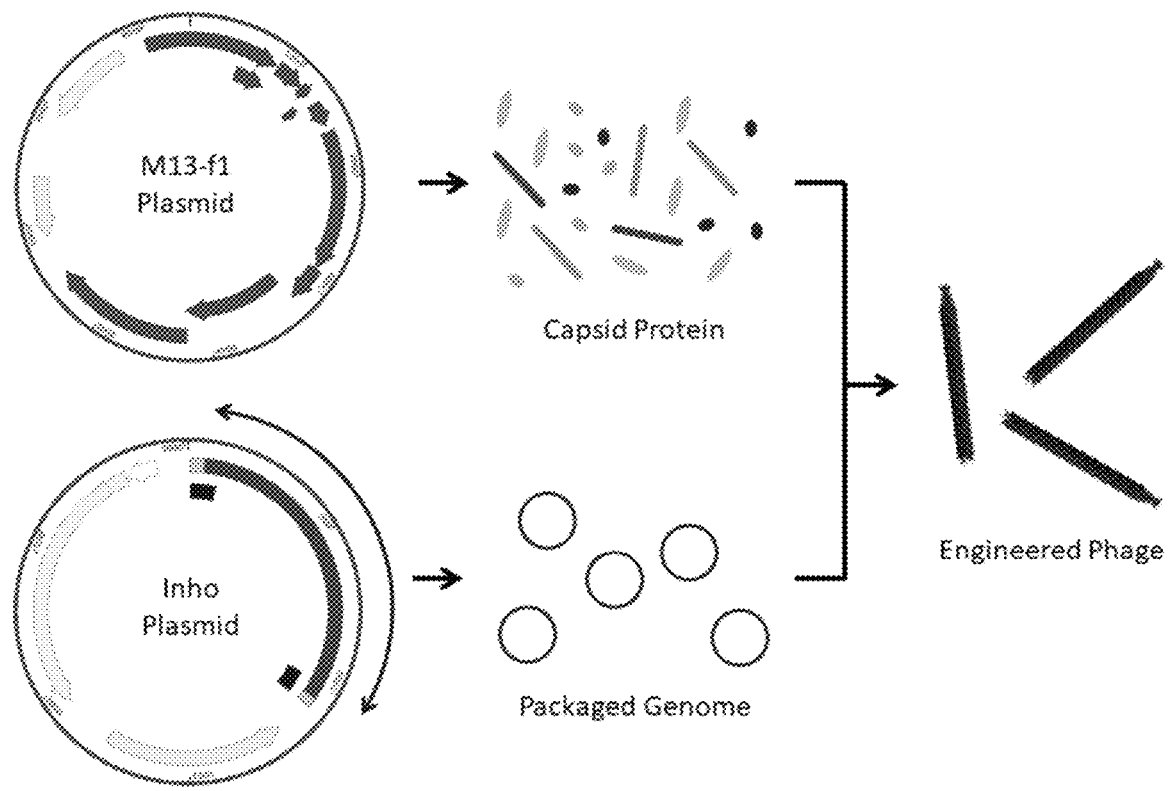
FIG. 1 shows a schematic of length-controllable engineered phage production. Inho plasmids produce specific length of circular single stranded DNAs (ssDNAs) when co-transformed with M13-f1 helper plasmids that express M13 phage proteins in *E. coli*. The ssDNAs are packaged with five capsid proteins, and the assembled engineered phage are extruded from the cells.

The origin of DNA replication of bacteriophage f1 contains a nucleotide sequence that is used for both initiation and termination of viral strand synthesis. The present disclosure provides modified versions of the nucleotide sequence of the origin of DNA replication that are used for either initiation or termination. These modified versions, referred to as engineered initiator and terminator sequences, provide tight and reproducible transcriptional control of any DNA sequence located between them, thereby enabling production of single-stranded DNA (ssDNA) having uniform length. The ability of these engineered initiator and terminator sequences to tightly regulate the size of produced DNA was quite surprising. Prior attempts to engineer these sequences were not able to accomplish the tight regulation over DNA production to achieve a sample of uniform length. Accordingly, the present disclosure provides methods and compositions for producing ssDNA having uniform length using engineered initiator and terminator sequences disclosed herein.

Methods and compositions for producing ssDNA having uniform length provided herein involve an engineered nucleic acid comprising an engineered initiator sequence, an engineered terminator sequence, and a DNA sequence of interest that may be produced as a ssDNA having uniform length according to methods described herein, and host cells comprising such engineered nucleic acids.

Engineered Nucleic Acids

Engineered nucleic acids of the present disclosure, in some embodiments, are useful for producing ssDNA having uniform length. In some embodiments, the engineered nucleic acid comprises an engineered initiator sequence and an engineered terminator sequence from a filamentous bacteriophage, and a DNA sequence of interest.

A "nucleic acid" is at least two nucleotides covalently linked together, and in some instances, may contain phosphodiester bonds (e.g., a phosphodiester "backbone"). "Engineered nucleic acids" include recombinant nucleic acids and synthetic nucleic acids. A "recombinant nucleic acid" refers to a molecule that is constructed by joining nucleic acid molecules, and typically, can replicate in a living cell. A "synthetic nucleic acid" refers to a molecule that is biologically synthesized, chemically synthesized, or by other means synthesized or amplified. A synthetic nucleic acid includes but is not limited to nucleic acids that are chemically modified or otherwise modified but can base pair with naturally-occurring nucleic acid molecules. Engineered nucleic acids may contain portions of nucleic acids that are naturally occurring, but as a whole, engineered nucleic acids do not occur naturally and require human intervention. In some embodiments, the engineered nucleic acid comprises a recombinant nucleic acid that is incorporated into a vector, an autonomously replicating plasmid, a bacteriophage, a virus, or into a genomic DNA of a prokaryote or eukaryote.

In some embodiments, the engineered nucleic acid comprises an engineered initiator sequence, and an engineered terminator sequence, and a DNA sequence of interest. In some embodiments, the engineered nucleic acid comprises a DNA sequence of interest that is located 3' to an engineered initiator sequence and 5' to an engineered terminator sequence. A DNA sequence of interest may be directly or indirectly linked to the engineered initiator and/or engineered terminator sequences. A DNA sequence of interest is considered to be directly linked to an engineered initiator sequence and an engineered terminator sequence when it is located between the engineered sequences in the absence of intervening nucleic acids. A DNA sequence of interest is considered to be indirectly linked to an engineered initiator sequence and an engineered terminator sequence when it is located between the engineered sequences in the presence of intervening nucleic acids.

In some embodiments, an engineered nucleic acid comprises a selectable marker. Examples of selectable markers include, without limitation, genes encoding proteins that increase or decrease either resistance or sensitivity to antibiotics (e.g., ampicillin resistance genes, kanamycin resistance genes, neomycin resistance genes, tetracycline resistance genes and chloramphenicol resistance genes) or other compounds. Additional examples of selectable markers include, without limitation, genes encoding proteins that enable the cell to grow in media deficient in an otherwise essential nutrient (auxotrophic markers). Other selectable markers may be used in accordance with the present disclosure.

Engineered nucleic acids may be single-stranded or double-stranded. In some embodiments, the engineered nucleic acid is single-stranded. In some embodiments, the engineered nucleic acid is double-stranded.

Engineered nucleic acids may be linear or circular. In some embodiments, the engineered nucleic acid is linear. In some embodiments, the engineered nucleic acid is circular.

Engineered nucleic acids may be introduced into host cells using any means known in the art, including, without limitation, transformation, transfection such as chemical transfection (e.g., calcium phosphate, cationic polymers, or liposomes) or non-chemical transfection (e.g., electroporation, sonoporation, impalefection, optical transfection, hydrodynamic transfection), and transduction (e.g., viral transduction).

Engineered nucleic acids of the present disclosure may be produced using standard molecular biology methods (see, e.g., Green and Sambrook, Molecular Cloning, A Laboratory Manual, 2012, Cold Spring Harbor Press). In some embodiments, engineered nucleic acids are produced using GIBSON ASSEMBLY® Cloning (see, e.g., Gibson, D. G. et al. Nature Methods, 343-345, 2009; and Gibson, D. G. et al. Nature Methods, 901-903, 2010, each of which is incorporated by reference herein). GIBSON ASSEMBLY® typically uses three enzymatic activities in a single-tube reaction: 5' exonuclease activity, the 3' extension activity of a DNA polymerase and DNA ligase activity. The 5' exonuclease activity chews back the 5' end of nucleic acid sequences and exposes the complementary sequence for annealing. The polymerase activity then fills in the gaps on the annealed domains. A DNA ligase then seals the nick and covalently links the DNA fragments together. The overlapping sequence of adjoining fragments is much longer than those used in Golden Gate Assembly, and therefore results in a higher percentage of correct assemblies. Other methods of producing engineered nucleic acids are known in the art and may be used in accordance with the present disclosure.

Engineered Initiator and Terminator Sequences

An engineered initiator sequence is a nucleic acid sequence from bacteriophage that has been modified to eliminate terminator function and maintain initiator function for producing single-stranded DNA (ssDNA) having uniform length. An engineered terminator sequence is a nucleic acid sequence from bacteriophage that has been modified to maintain terminator function and eliminate initiator function for producing single-stranded DNA (ssDNA) having uniform length. Accordingly, the engineered initiator sequence and the engineered terminator sequence differ from a naturally occurring nucleic acid sequence of an origin of DNA replication of a bacteriophage.

In some embodiments, the engineered initiator sequence comprises a modified nucleic acid sequence of an origin of DNA replication of a bacteriophage. In some embodiments, the engineered initiator sequence comprises a modified nucleic acid sequence of an origin of DNA replication of a filamentous bacteriophage. In some embodiments, the engineered initiator sequence comprises a modified nucleic acid sequence of an origin of DNA replication of a bacteriophage f1. In some embodiments, the engineered initiator sequence comprises a modified nucleic acid sequence of an origin of DNA replication of a bacteriophage M13. In some embodiments, the engineered initiator sequence comprises a modified nucleic acid sequence of an origin of DNA replication of a bacteriophage fd.

In some embodiments, the engineered terminator sequence comprises a modified nucleic acid sequence of an origin of DNA replication of a bacteriophage. In some embodiments, the engineered terminator sequence comprises a modified nucleic acid sequence of an origin of DNA replication of a filamentous bacteriophage. In some embodiments, the engineered terminator sequence comprises a modified nucleic acid sequence of an origin of DNA replication of a bacteriophage f1. In some embodiments, the engineered terminator sequence comprises a modified nucleic acid sequence of an origin of DNA replication of a bacteriophage M13. In some embodiments, the engineered terminator sequence comprises a modified nucleic acid sequence of an origin of DNA replication of a bacteriophage fd.

In some embodiments, the engineered initiator sequence comprises at least one modified nucleotide as compared to a nucleic acid sequence of an origin of DNA replication of a bacteriophage. In some embodiments, the engineered terminator sequence comprises at least one modified nucleotide as compared to a nucleic acid sequence of an origin of DNA replication of a bacteriophage. Non-limiting examples of a modified nucleotide include a deletion, an insertion, and a substitution of one nucleotide (e.g., adenosine) for another nucleotide (e.g., cytosine). A modified nucleic acid sequence differs from a corresponding native nucleic acid sequence by at least 1 nucleotide.

In some embodiments, the engineered initiator sequence comprises at least two, at least three, at least four, at least five, at least six, at least seven, at least eight, at least nine, at least ten, at least eleven, at least twelve, at least thirteen, at least fourteen, at least fifteen, at least twenty, or at least twenty five modified nucleotides as compared to a nucleic acid sequence of an origin of DNA replication of a bacteriophage.

In some embodiments, the engineered terminator sequence comprises at least two, at least three, at least four, at least five, at least six, at least seven, at least eight, at least nine, at least ten, at least eleven, at least twelve, at least thirteen, at least fourteen, at least fifteen, at least twenty, or at least twenty five modified nucleotides as compared to a nucleic acid sequence of an origin of DNA replication of a bacteriophage.

In some embodiments, the engineered initiator sequence comprises an insertion as compared to a nucleic acid sequence of an origin of DNA replication of a bacteriophage. In some embodiments, the engineered initiator sequence comprises a deletion as compared to a nucleic acid sequence of an origin of DNA replication of a bacteriophage. In some embodiments, the engineered initiator sequence comprises a substitution as compared to a nucleic acid sequence of an origin of DNA replication of a bacteriophage.

In some embodiments, the engineered terminator sequence comprises an insertion as compared to a nucleic acid sequence of an origin of DNA replication of a bacteriophage. In some embodiments, the engineered terminator sequence comprises a deletion as compared to a nucleic acid sequence of an origin of DNA replication of a bacteriophage. In some embodiments, the engineered terminator sequence comprises a substitution as compared to a nucleic acid sequence of an origin of DNA replication of a bacteriophage.

In some embodiments, the engineered initiator sequence comprises a combination of modifications (e.g., a deletion and a substitution) as compared to a nucleic acid sequence of an origin of DNA replication of a bacteriophage. In some embodiments, the engineered initiator sequence comprises a deletion and a substitution as compared to a nucleic acid sequence of an origin of DNA replication of a bacteriophage. In some embodiments, the engineered initiator sequence comprises an insertion and a substitution as compared to a nucleic acid sequence of an origin of DNA replication of a bacteriophage. In some embodiments, the engineered initiator sequence comprises an insertion and a deletion as compared to a nucleic acid sequence of an origin of DNA replication of a bacteriophage.

In some embodiments, the engineered terminator sequence comprises a combination of modifications (e.g., a deletion and a substitution) as compared to a nucleic acid sequence of an origin of DNA replication of a bacteriophage. In some embodiments, the engineered terminator sequence comprises a deletion and a substitution as compared to a nucleic acid sequence of an origin of DNA replication of a bacteriophage. In some embodiments, the engineered terminator sequence comprises an insertion and a substitution as compared to a nucleic acid sequence of an origin of DNA replication of a bacteriophage. In some embodiments, the engineered terminator sequence comprises an insertion and a deletion as compared to a nucleic acid sequence of an origin of DNA replication of a bacteriophage.

Examples of an engineered initiator sequence and an engineered terminator sequence from a bacteriophage f1 are provided in Table 1.

TABLE 1

Examples of engineered initiator and terminator sequences from bacteriophage f1.

| Name | Sequence | SEQ ID NO: |
|---|---|---|
| Origin of DNA replication of a bacteriophage f1 | GAGTCCACGTTCTTTAATAGT GGACTCTTGTTCCAAACTGGA ACAACACTC | 1 |
| Engineered initiator sequence | CTTTAATAGTGGACTCTTGT TCCAAACTGGAACAACACTC | 2 |
| Engineered terminator sequence | GAGTCCACGTTCTTTAATAGTGG ACTCTTGTTCCAAACAACACTC | 3 |

In some embodiments, the engineered initiator sequence comprises a nucleic acid sequence having at least 75% identity to a nucleic acid sequence of an origin of DNA replication of a bacteriophage provided in SEQ ID NO: 1. In some embodiments, the engineered initiator sequence comprises a nucleic acid sequence having at least 75%, at least 80%, at least 85%, at least 90%, at least 95%, at least 96%, at least 97%, at least 98%, or at least 99% identity to SEQ ID NO: 1.

In some embodiments, the engineered terminator sequence comprises a nucleic acid sequence having at least 75% identity to a nucleic acid sequence of an origin of DNA replication of a bacteriophage provided in SEQ ID NO: 1. In some embodiments, the engineered terminator sequence comprises a nucleic acid sequence having at least 75%, at least 80%, at least 85%, at least 90%, at least 95%, at least 96%, at least 97%, at least 98%, or at least 99% identity to SEQ ID NO: 1.

In some embodiments, the engineered initiator sequence comprises a nucleic acid sequence having at least 75% identity to SEQ ID NO: 2. In some embodiments, the engineered initiator sequence comprises a nucleic acid sequence having at least 80%, at least 85%, at least 90%, at least 95%, at least 96%, at least 97%, at least 98%, or at least 99% identity to SEQ ID NO: 2. In some embodiments, the engineered initiator sequence comprises SEQ ID NO: 2. In some embodiments, the engineered initiator sequence consists of SEQ ID NO: 2. In some embodiments, the engineered initiator sequence is SEQ ID NO: 2.

In some embodiments, the engineered terminator sequence comprises a nucleic acid sequence having at least 75% identity to SEQ ID NO: 3. In some embodiments, the engineered terminator sequence comprises a nucleic acid sequence having at least 80%, at least 85%, at least 90%, at least 95%, at least 96%, at least 97%, at least 98%, or at least 99% identity to SEQ ID NO: 3. In some embodiments, the engineered terminator sequence comprises SEQ ID NO: 3. In some embodiments, the engineered terminator sequence consists of SEQ ID NO: 3. In some embodiments, the engineered terminator sequence is SEQ ID NO: 3.

DNA Sequences of Interest

Methods and compositions of the present disclosure encompass any DNA sequence of interest. In some embodiments, the DNA sequence of interest comprises a genomic DNA sequence. In some embodiments, the DNA sequence of interest comprises a coding DNA sequence (e.g., a protein coding sequence). In some embodiments, the DNA sequence of interest comprises a non-coding DNA sequence (e.g., a non-protein-coding DNA sequence).

A DNA sequence of interest provided herein may comprise any length of sequence. In some embodiments, a DNA sequence of interest has a length of 100 nucleotides to 20,000 nucleotides, or more. For example, a DNA sequence of interest may have a length of 100 to 19,000 nucleotides, 100 to 18,000 nucleotides, 100 to 17,000 nucleotides, 100 to 16,000 nucleotides, 100 to 15,000 nucleotides, 100 to 14,000 nucleotides, 100 to 13,000 nucleotides, 100 to 12,000 nucleotides, 100 to 11,000 nucleotides, 100 to 10,000 nucleotides, 100 to 9000 nucleotides, 100 to 8000 nucleotides, 100 to 7000 nucleotides, 100 to 6000 nucleotides, 100 to 5000 nucleotides, 100 to 4000 nucleotides, 100 to 3000 nucleotides, 100 to 2000 nucleotides, or 100 to 1000 nucleotides. In some embodiments, a DNA sequence of interest has a length of 1000 to 19,000 nucleotides, 1000 to 18,000 nucleotides, 1000 to 17,000 nucleotides, 1000 to 16,000 nucleotides, 1000 to 15,000 nucleotides, 1000 to 14,000 nucleotides, 1000 to 13,000 nucleotides, 1000 to 12,000 nucleotides, 1000 to 11,000 nucleotides, 1000 to 10000 nucleotides, 1000 to 9000 nucleotides, 1000 to 8000 nucleotides, 1000 to 7000 nucleotides, 1000 to 6000 nucleotides, 1000 to 5000 nucleotides, 1000 to 4000 nucleotides, 1000 to 3000 nucleotides, 1000 to 2000 nucleotides, 2000 to 10000 nucleotides, 2000 to 9000 nucleotides, 2000 to 8000 nucleotides, 2000 to 7000 nucleotides, 2000 to 6000 nucleotides, 2000 to 5000 nucleotides, 2000 to 4000 nucleotides, or 2000 to 3000 nucleotides. In some embodiments, a DNA sequence of interest may have a length of at least 100, at least 200, at least 300, at least 400, at least 500, at least 600, at least 700, at least 800, at least 900, at least at least 1000, at least 1100, at least 1200, at least 1300, at least 1400, at least 1500, at least 1600, at least 1700, at least 1800, at least 1900, at least 2000, at least 2100, at least 2200, at least 2300, at least 2400, at least 2500, at least 2600, at least 2700, at least 2800, at least 2900, at least 3100, at least 3200, at least 3300, at least 3400, at least 3500, at least 3600, at least 3700, at least 3800, at least 3900, at least 4100, at least 4200, at least 4300, at least 4400, at least 4500, at least 4600, at least 4700, at least 4800, at least 4900, at least 5100, at least 5200, at least 5300, at least 5400, at least 5500, at least 5600, at least 5700, at least 5800, at least 5900, at least 6600, at least 6200, at least 6300, at least 6400, at least 6500, at least 6600, at least 6700, at least 6800, at least 6900, at least 7100, at least 7200, at least 7300, at least 7400, at least 7500, at least 7600, at least 7700, at least 7800, at least 7900, at least 8100, at least 8200, at least 8300, at least 8400, at least 8500, at least 8600, at least 8700, at least 8800, at least 8900, at least 9100, at least 9200, at least 9300, at least 9400, at least 9500, at least 9600, at least 9700, at least 9800, at least 9900, at least 10,000, at least 10,100, at least 10,200, at least 10,300, at least 10,400, at least 10,500, at least 10,600, at least 10,700, at least 10,800, at least 10,900, at least 11,000, at least 11,100, at least 11,200, at least 11,300, at least 11,400, at least 11,500, at least 11,600, at least 11,700, at least 11,800, at least 11,900, at least 12,000, at least 12,100, at least 12,200, at least 12,300, at least 12,400, at least 12,500, at least 12,600, at least 12,700, at least 12,800, at least 12,900, at least 13,000, at least 13,100, at least 13,200, at least 13,300, at least 13,400, at least 13,500, at least 13,600, at least 13,700, at least 13,800, at least 13,900, at least 14,000, at least 14,100, at least 14,200, at least 14,300, at least 14,400, at least 14,500, at least 14,600, at least 14,700, at least 14,800, at least 14,900, at least 15,000, at least 15,100, at least 15,200, at least 15,300, at least 15,400, at least 15,500, at least 15,600, at least 15,700, at least 15,800, at least 15,900, at least 16,000, at least 16,100, at least 16,200, at least 16,300, at least 16,400, at least 16,500, at least 16,600, at least 16,700, at least 16,800, at least 16,900, at least 17,000, at least 17,100, at least 17,200, at least 17,300, at least 17,400, at least 17,500, at least 17,600, at least 17,700, at least 17,800, at least 17,900, at least 18,000, at least 18,100, at least 18,200, at least 18,300, at least 18,400, at least 18,500, at least 18,600, at least 18,700, at least 18,800, at least 18,900, at least 19,000, at least 19,100, at least 19,200, at least 19,300, at least 19,400, at least 19,500, at least 19,600, at least 19,700, at least 19,800, at least 19,900, or at least 20,000 nucleotides and each with an optional upper limit of 10,100 nucleotides.

Host Cells

Host cells of the present disclosure, in some embodiments, are useful for producing ssDNA sequences having uniform length using engineered nucleic acids described herein. Accordingly, host cells provided herein comprise at least one engineered nucleic acid, and therefore are structurally and/or functionally distinct from their naturally-occurring counterparts. In some embodiments, a host cell comprises an engineered nucleic acid.

A host cell "expresses" a product (e.g., a ssDNA) if the product, encoded by a nucleic acid (e.g., an engineered nucleic acid), is produced in the cell. It is known in the art that gene expression refers to the process by which genetic instructions in the form of a nucleic acid are used to synthesize a product, such as a ssDNA or a protein.

In some embodiments, a host cell further comprises a nucleic acid helper plasmid. Nucleic acid helper plasmid refers to a plasmid that expresses at least one bacteriophage protein in a host cell. In some embodiments, the nucleic acid helper plasmid expresses at least one bacteriophage protein capable of encapsulating ssDNA. In some embodiments, the nucleic acid helper plasmid expresses at least one bacteriophage protein capable of extruding encapsulated ssDNA from the host cell.

Nucleic acid helper plasmids described herein may express a plurality of bacteriophage proteins. In some embodiments, the plurality of bacteriophage proteins comprises at least one, at least two, at least three, at least four, at least five, at least six, at least seven, at least eight, at least nine, at least ten, or at least eleven bacteriophage proteins. In some embodiments, the plurality of bacteriophage proteins are selected from the group consisting of P1, P2, P3, P4, P5, P6, P7, P8, P9, P10, and P11. In some embodiments, the plurality of proteins comprises P3, P6, P7, P8, and P9.

Nucleic acid helper plasmids as described herein may or may not comprise a packaging signal. In some embodiments, the nucleic acid helper plasmid comprises a packaging signal. In some embodiments, the nucleic acid helper plasmid lacks a packaging signal.

In some embodiments, the nucleic acid helper plasmid comprises at least one additional functional element that can be incorporated into or onto the ssDNA of interest. In some embodiments, the engineered nucleic acid comprises at least one additional functional element that can be incorporated into or onto the ssDNA of interest. The at least one additional functional element can be, for example, single-guide- or crispr-RNAs (sgRNA or crRNA), anti-sense DNA, anti-sense RNA, at least one protein, or a combination thereof. The anti-sense RNA can be, for example, RNAi, miRNA, piRNA or siRNA. The at least one protein can be therapeutic, non-therapeutic, or a combination thereof. In some embodiments, the at least one protein comprises a Cas protein, TAL effector protein, or zinc-finger protein. In some embodiments, the host cells also express single-guide- or crispr-RNAs (sgRNA or crRNA) alone or in combination with a Cas protein. Thus, compositions and methods provided herein may be used to package a gene editing composition including a CRISPR/Cas system into a ssDNA.

In some embodiments, a host cell expresses a selectable marker. Selectable markers are typically used to select host cells that have taken up and expressed an engineered nucleic acid following transfection of the cell (or following other procedure used to introduce foreign nucleic acid into the cell).

Host cells may be prokaryotic cells or eukaryotic cells. In some embodiments, engineered cells are bacterial cells, yeast cells, insect cells, mammalian cells, or other types of cells.

Bacterial cells of the present disclosure include, without limitation, *Escherichia* spp., *Streptomyces* spp., *Zymomonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., and *Pantoea* spp. In some embodiments, host cells of the present disclosure are *Escherichia coli* cells.

Methods for Producing Single-Stranded DNA (ssDNA)

Methods and compositions provided herein, in some embodiments, provide engineered phages that each comprise a ssDNA that is substantially the same length. Extracting the ssDNA from the engineered phages produces ssDNA having uniform length. As used herein, "ssDNA having uniform length" refers to ssDNA that is substantially the same length.

In some embodiments, methods for producing ssDNA having uniform length comprise (a) culturing a host cell provided herein under conditions suitable for producing the ssDNA encoded by the DNA sequence of interest in the engineered nucleic acid and for producing the plurality of bacteriophage proteins from the nucleic acid helper plasmid, (b) allowing the ssDNA and the plurality of bacteriophage proteins to assemble into an engineered phage; and (c) collecting the engineered phage.

"Culturing" refers to the process by which host cells are grown under controlled conditions, typically outside of their natural environment. For example, host cells, such as host cells comprising an engineered nucleic acid, may be grown as a cell suspension in liquid nutrient broth, also referred to as liquid "culture medium."

Examples of commonly used bacterial *E. coli* growth media include, but are not limited to, LB (Lysogeny Broth) Miller broth (1% NaCl): 1% peptone, 0.5% yeast extract, and 1% NaCl; LB (Lysogeny Broth) Lennox Broth (0.5% NaCl): 1% peptone, 0.5% yeast extract, and 0.5% NaCl; SOB medium (Super Optimal Broth): 2% peptone, 0.5% Yeast extract, 10 mM NaCl, 2.5 mM KCl, 10 mM $MgCl_2$, 10 mM $MgSO_4$; SOC medium (Super Optimal broth with Catabolic repressor): SOB+20 mM glucose; 2×YT broth (2× Yeast extract and Tryptone): 1.6% peptone, 1% yeast extract, and 0.5% NaCl; TB (Terrific Broth) medium: 1.2% peptone, 2.4% yeast extract, 72 mM $K_2HPO_4$, 17 mM $KH_2PO_4$ and 0.4% glycerol; and SB (Super Broth) medium: 3.2% peptone, 2% yeast extract, and 0.5% NaCl and or Korz medium (Korz, D J et al. 1995). Examples of high density bacterial *E. coli* growth media include, but are not limited to, DNAGro™ medium, ProGro™ medium, AutoX™ medium, DetoX™ medium, InduX™ medium, and SecPro™ medium.

In some embodiments, host cells are cultured under conditions that result in expression of a ssDNA. Such culture conditions may depend on the particular ssDNA being expressed and the desired amount of the ssDNA produced.

In some embodiments, host cells are cultured at a temperature of 30° C. to 40° C. For example, host cells may be cultured at a temperature of 30° C., 31° C., 32° C., 33° C., 34° C., 35° C., 36° C., 37° C., 38° C., 39° C. or 40° C. Typically, host cells, such as $E.\ coli$ cells comprising an engineered nucleic acid provided herein, are cultured at a temperature of 37° C.

In some embodiments, host cells are cultured for a period of time of 12 hours to 72 hours, or more. For example, host cells may be cultured for a period of time of 12, 18, 24, 30, 36, 42, 48, 54, 60, 66, or 72 hours. Typically, host cells, such as $E.\ coli$ cells comprising an engineered nucleic acid provided herein, are cultured for a period of time of 12 to 24 hours. In some embodiments, engineered cells are cultured for 12 to 24 hours at a temperature of 37° C.

In some embodiments, host cells are cultured (e.g., in liquid cell culture medium) to an optical density, measured at a wavelength of 600 nm ($OD_{600}$), of 5 to 200. In some embodiments, host cells are cultured to an $OD_{600}$ of 5, 10, 15, 20, 25, 50, 75, 100, 150, or 200. In some embodiments, host cells are cultured to an optical density, measured at a wavelength of 600 nm ($OD_{600}$), of 0.1 to 5. In some embodiments, host cells are cultured to an $OD_{600}$ of 0.1, 0.2, 0.3, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, or 5.

In some embodiments, host cells are cultured to a density of $1 \times 10^8$ (OD<1) to $2 \times 10^{11}$ (OD ~200) viable cells/ml cell culture medium. In some embodiments, host cells are cultured to a density of $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, or $2 \times 10^{11}$ viable cells/ml. (Conversion factor: OD $1 = 8 \times 10^8$ cells/ml).

In some embodiments, host cells are cultured in a bioreactor. A bioreactor refers to a container in which cells are cultured, such as a culture flask, a dish, or a bag that may be single-use (disposable), autoclavable, or sterilizable. The bioreactor may be made of glass, or it may be polymer-based, or it may be made of other materials.

Methods of the present disclosure encompass large-scale production of ssDNA. For large-scale production methods, host cells may be grown in liquid culture medium in a volume of 5 liters (L) to 250,000 L, or more. In some embodiments, host cells may be grown in liquid culture medium in a volume of greater than (or equal to) 10 L, 100 L, 1000 L, 10000 L, or 100000 L. In some embodiments, host cells are grown in liquid culture medium in a volume of 5 L, 10 L, 15 L, 20 L, 25 L, 30 L, 35 L, 40 L, 45 L, 50 L, 100 L, 500 L, 1000 L, 5000 L, 10000 L, 100000 L, 150000 L, 200000 L, 250000 L, or more. In some embodiments, host cells may be grown in liquid culture medium in a volume of 5 L to 10 L, 5 L to 15 L, 5 L to 20 L, 5 L to 25 L, 5 L to 30 L, 5 L to 35 L, 5 L to 40 L, 5 L to 45 L, 10 L to 15 L, 10 L to 20 L, 10 L to 25 L, 20 L to 30 L, 10 L to 35 L, 10 L to 40 L, 10 L to 45 L, 10 L to 50 L, 15 L to 20 L, 15 L to 25 L, 15 L to 30 L, 15 L to 35 L, 15 L to 40 L, 15 L to 45 L, or 15 to 50 L. In some embodiments, host cells may be grown in liquid culture medium in a volume of 100 L to 300000 L, 100 L to 200000 L, or 100 L to 100000 L.

Typically, culturing of host cell is followed by collecting engineered phage comprising ssDNA. In some embodiments, collecting engineered phage comprises collecting supernatant comprising the engineered phage. In some embodiments, supernatant comprising engineered phage is collected using centrifugation. In some embodiments, supernatant comprising engineered phage is collected using tangential flow filtration.

Methods provided herein encompass extracting ssDNA from engineered phages. In some embodiments, extracting ssDNA from engineered phages comprises polyethylene glycol (PEG) extraction. In some embodiments, extracting ssDNA from engineered phages comprises phenol-chloroform extraction. In some embodiments, extracting ssDNA from engineered phages comprises isopropanol extraction.

Methods provided herein, in some embodiments, yield ssDNA at a concentration of 1-50 g/L. In some embodiments, methods provided herein yield ssDNA at a concentration of between 5-50 g/L, 10-50 g/L, 15-50 g/L, 20-50 g/L, 25-50 g/L, 30-50 g/L, 35-50 g/L, 40-50 g/L, or 45-50 g/L. In some embodiments, methods provided herein yield ssDNA at a concentration of between 1-45 g/L, 1-40 g/L, 1-35 g/L, 1-30 g/L, 1-25 g/L, 1-20 g/L, 1-15 g/L, 1-10 g/L, or 1-5 g/L.

In some embodiments, methods provided herein produce ssDNA from a DNA sequence of interest located between an engineered initiator sequence and an engineered terminator sequence in an engineered nucleic acid. In some embodiments, at least 80% of ssDNA produced from a DNA sequence of interest has the same length as the DNA sequence of interest. In some embodiments, at least 85%, at least 90%, at least 91%, at least 92%, at least 93%, at least 94%, at least 95%, at least 96%, at least 97%, at least 98%, or at least 99% of ssDNA produced from a DNA sequence of interest has the same length as the DNA sequence of interest.

Methods provided herein encompass producing ssDNA having any sequence. In some embodiments, the ssDNA comprises a genomic DNA sequence. In some embodiments, the ssDNA comprises a coding DNA sequence. In some embodiments, the ssDNA comprises a non-coding DNA sequence.

Methods provided herein encompass producing ssDNA having any length. In some embodiments, ssDNA has a length of 100 nucleotides to 20,000 nucleotides, or more. For example, ssDNA may have a length of 100 to 19,000 nucleotides, 100 to 18,000 nucleotides, 100 to 17,000 nucleotides, 100 to 16,000 nucleotides, 100 to 15,000 nucleotides, 100 to 14,000 nucleotides, 100 to 13,000 nucleotides, 100 to 12,000 nucleotides, 100 to 11,000 nucleotides, 100 to 10,000 nucleotides, 100 to 9000 nucleotides, 100 to 8000 nucleotides, 100 to 7000 nucleotides, 100 to 6000 nucleotides, 100 to 5000 nucleotides, 100 to 4000 nucleotides, 100 to 3000 nucleotides, 100 to 2000 nucleotides, or 100 to 1000 nucleotides. In some embodiments, ssDNA has a length of 1000 to 10000 nucleotides, 1000 to 9000 nucleotides, 1000 to 8000 nucleotides, 1000 to 7000 nucleotides, 1000 to 6000 nucleotides, 1000 to 5000 nucleotides, 1000 to 4000 nucleotides, 1000 to 3000 nucleotides, 1000 to 2000 nucleotides, 2000 to 10000 nucleotides, 2000 to 9000 nucleotides, 2000 to 8000 nucleotides, 2000 to 7000 nucleotides, 2000 to 6000 nucleotides, 2000 to 5000 nucleotides, 2000 to 4000 nucleotides, or 2000 to 3000 nucleotides.

In some embodiments, ssDNA may have a length of at least 100, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, at least 2000, at least 2100, at least 2200, at least 2300, at least 2400, at least 2500, at least 2600, at least 2700, at least 2800, at least 2900, at least 3100, at least 3200, at least 3300, at least 3400, at least 3500, at least 3600, at least 3700, at least 3800, at least 3900, at least 4100, at least 4200, at least 4300, at least 4400, at least 4500, at least 4600, at least 4700, at least 4800, at least 4900, at least 5100, at least 5200, at least 5300, at least 5400, at least 5500, at least 5600, at least 5700, at least 5800, at least 5900, at least 6600, at least 6200, at least 6300, at least 6400, at least 6500, at least 6600, at least 6700, at least 6800, at least 6900, at least 7100, at least 7200, at least 7300, at least 7400, at least 7500, at least 7600, at least 7700, at least 7800, at least 7900, at least 8100, at least 8200, at least 8300, at least 8400, at least 8500, at least 8600, at least 8700, at least 8800, at least 8900, at least 9100, at least 9200, at least 9300, at least 9400, at least 9500, at least 9600, at least 9700, at least 9800, at least 9900, at least 10,000, at least 10,100, at least 10,200, at least 10,300, at least 10,400, at least 10,500, at least 10,600, at least 10,700, at least 10,800, at least 10,900, at least 11,000, at least 11,100, at least 11,200, at least 11,300, at least 11,400, at least 11,500, at least 11,600, at least 11,700, at least 11,800, at least 11,900, at least 12,000, at least 12,100, at least 12,200, at least 12,300, at least 12,400, at least 12,500, at least 12,600, at least 12,700, at least 12,800, at least 12,900, at least 13,000, at least 13,100, at least 13,200, at least 13,300, at least 13,400, at least 13,500, at least 13,600, at least 13,700, at least 13,800, at least 13,900, at least 14,000, at least 14,100, at least 14,200, at least 14,300, at least 14,400, at least 14,500, at least 14,600, at least 14,700, at least 14,800, at least 14,900, at least 15,000, at least 15,100, at least 15,200, at least 15,300, at least 15,400, at least 15,500, at least 15,600, at least 15,700, at least 15,800, at least 15,900, at least 16,000, at least 16,100, at least 16,200, at least 16,300, at least 16,400, at least 16,500, at least 16,600, at least 16,700, at least 16,800, at least 16,900, at least 17,000, at least 17,100, at least 17,200, at least 17,300, at least 17,400, at least 17,500, at least 17,600, at least 17,700, at least 17,800, at least 17,900, at least 18,000, at least 18,100, at least 18,200, at least 18,300, at least 18,400, at least 18,500, at least 18,600, at least 18,700, at least 18,800, at least 18,900, at least 19,000, at least 19,100, at least 19,200, at least 19,300, at least 19,400, at least 19,500, at least 19,600, at least 19,700, at least 19,800, at least 19,900, or at least 20,000 nucleotides.

Once the ssDNA oligonucleotide is produced in the cell it may be used in the cell or isolated from the cell. ssDNA oligonucleotides isolated from a cell may be used for any purpose that ssDNA oligonucleotides are used for. For instance, they may be therapeutic oligonucleotides that can be administered to other cells or in vivo to a subject such as an animal or human. Alternatively they may be used in research or to build structures such as nanostructures or used in a method of DNA origami.

It should be appreciated that the ssDNA oligonucleotides described herein may be designed to produce any matter of nucleic acid based nanostructures. Additionally, the system generates unique elements including DNA/RNA hybrids that may be used for the development of novel structural elements.

Aspects of the disclosure relate to methods for making a nucleic acid nanostructure by synthesizing one or more ssDNA oligonucleotides in a cell and subjecting the ssDNA oligonucleotides to conditions that promote DNA-directed self-assembly to produce a nucleic acid nanostructure. In some embodiments a set of oligonucleotides is synthesized in the cell by transforming the cell with at least one first nucleic acid, and transforming the cell with at least one second nucleic acid using the engineered molecules disclosed herein. In some embodiments, the ssDNA oligonucleotides are isolated from the cell and purified.

A DNA nanostructure is a structure made from one or more nucleic acids including oligonucleotides and longer nucleic acids and combinations thereof using one or more sticky ends of the nucleic acids to assemble a three dimensional structure driven by programmed base pairing. The term "programmed base pairing" indicates that the sticky ends of the different nucleic acids are designed to ensure interactions of specific nucleic acids through their complementary sticky ends, thus programming the position of the nucleic acid within the structure. A predetermined position indicates that the ultimate position of each nucleic acid in the structure is based on the sequence and position of its sticky ends and the sequence and position of the sticky ends of the other nucleic acid building blocks in the structure, such that the plurality of nucleic acids can only assemble in one specific way.

The methods of the invention can be used (either isolated or within the cell in which it is produced) for the nanofabrication of complex structures and useful devices, essentially of any shape, structure or size.

The nucleic acids used in generating the nanostructures typically have a core and sticky ends for building the structure. The core may include, for instance, 4 arm branch junctions, 3 arm branch junctions, double crossovers, triple crossovers, parallelograms, 8 helix bundles, 6-tube formations, and structures assembled using one or more long strands of nucleic acid that are folded with the help of smaller helper strands. The core may also include protein specific binding sites or other regulatory or non-regulatory elements. The choice of which type of nucleic acid to use is within the level of skill in the art.

Nanostructures may be made for instance by DNA origami techniques, which are well known in the art. The invention also encompasses nanostructures made according to the invention. The nanostructures may have the shape size, consistency, components of any known nanostructure but they are made by the in vivo synthesized ssDNA oligonucleotides. The nanostructure may also be a nanorobot, which can carry out various functions within a cell.

Some aspects of the invention relate to a method of modulating gene expression in a cell by synthesizing a DNA oligonucleotide in the cell where the DNA oligonucleotide is a regulatory oligonucleotide, and causes the cell to modulate gene expression with the DNA oligonucleotide. In some embodiments, the DNA oligonucleotide is an antisense oligonucleotide.

EXAMPLES

In order that the invention described herein may be more fully understood, the following examples are set forth. The examples described in this application are offered to illustrate the methods and compositions provided herein and are not to be construed in any ways as limiting their scope.

Example 1: Materials and Methods

Strains and Culture Media

*E. coli* XL1-Blue (Agilent Technologies, Santa Clara, CA, USA) was used for all molecular cloning and M13 phage culture. LB-Miller media (BD, Franklin Lakes, NJ, USA) and LB+1.5% agar (BD, Franklin Lakes, NJ, USA) plates were used for molecular cloning and M13 phage culture. SOC outgrowth media (New England BioLabs, Ipswich, MA, USA) was used for transformation recovery.

Production of Engineered M13 Phage

Genetically engineered Inho and M13-f1 plasmids were co-transformed in *E. coli* XL1-Blue, and cultured on LB-agar plates containing ampicillin (100 mg/L) and kanamycin (50 mg/L) overnight. The grown single colony was picked and cultured in 70 mL LB media containing ampicillin and kanamycin overnight. Cultures were centrifuged at 10,000 g at 4° C. for 30 min, and the supernatant containing engineered phage was collected. For phage purification, 20 mL 50% PEG8000 (Sigma Aldrich, St. Louis, MO, USA) (w/v) and 10 mL 5M NaCl solution were mixed. The mixture was incubated at 4° C. for 24 hours, and centrifuged at 20,000 g at 4° C. for 30 min. Supernatant was removed and the phage pellet was resuspended in 2 mL 1×TAE buffer.

Extraction of ssDNA from Engineered M13 Phage

1 µL DNase I solution (2500 U/mL, Thermo Fisher Scientific, Waltham, MA, USA) was applied to the phage solution with 50 mM $MgCl_2$ and 13 mM $CaCl_2$), and incubated at 37° C. for 10 min to remove all unwanted DNA. To inactivate Dnase I, the phage mixture was heated at 65° C. for 10 min. After Dnase I treatment, the ssDNA can be isolated from engineered phage using QIAprep Spin M13 kit (Qiagen, Germantown, MD, USA) or other standard ethanol precipitation protocols.

TEM Characterization of Engineered Phage

Sizes of engineered phage were measured by JEOL 2010 Advanced High Performance TEM with an acceleration voltage of 200 kV. 10 µL phage solution was deposited on a TEM copper grid with a carbon thin film and incubated for 3 min. 10 µL of 10-fold diluted uranyl acetate alternative solution (Ted Pella, Redding, CA, USA) was deposited on the sample and incubated for 20 min. The excess solution was soaked before characterization. The sizes of engineered phage in TEM images were analyzed by ImageJ.

Example 2: Systems for Producing Engineered Phages Having ssDNA of a Uniform Length Filamentous M13 phage are a family of ssDNA containing viruses that infect only gram-negative bacteria. Upon infecting *E. coli*, the M13 single stranded genome, which expresses M13 phage proteins, is replicated through plus (+) strand synthesis in a rolling-circle fashion due to the existence of the f1 replication origin (f1-ori). The replicated ssDNA is assembled with capsid proteins in cell membranes, and phage particles are extruded from the host cells. In systems provided herein, functions of M13 phage genome are divided into two plasmids—Inho phagemid and M13-f1 helper plasmid. As shown in FIG. 1, the Inho phagemids produce circular ssDNA in the presence of M13 phage proteins, and the M13-f1 helper plasmids express all phage proteins for M13 phage assembly and DNA replication. There are two engineered f1-ori sequences (squares) in the Inho plasmids, and the lines between the two f1-ori sequences becomes the single-stranded genome, which dictates the size of engineered phage. The generated ssDNA genomes are encapsulated with major coat protein (P8) and minor coat proteins (P3, P6, P7, P9) and extruded from the bacterial body.

After purification from the *E. coli* media, monodisperse engineered M13 phage particles are obtained. The length of these phages are directly related to the size of the encapsulated ssDNA, which is engineered as desired via the Inho phagemid. Accordingly, systems described herein provide unfettered flexibility over bases and lengths of ssDNA that can then be extracted from the collected engineered phage.

Figure 2:
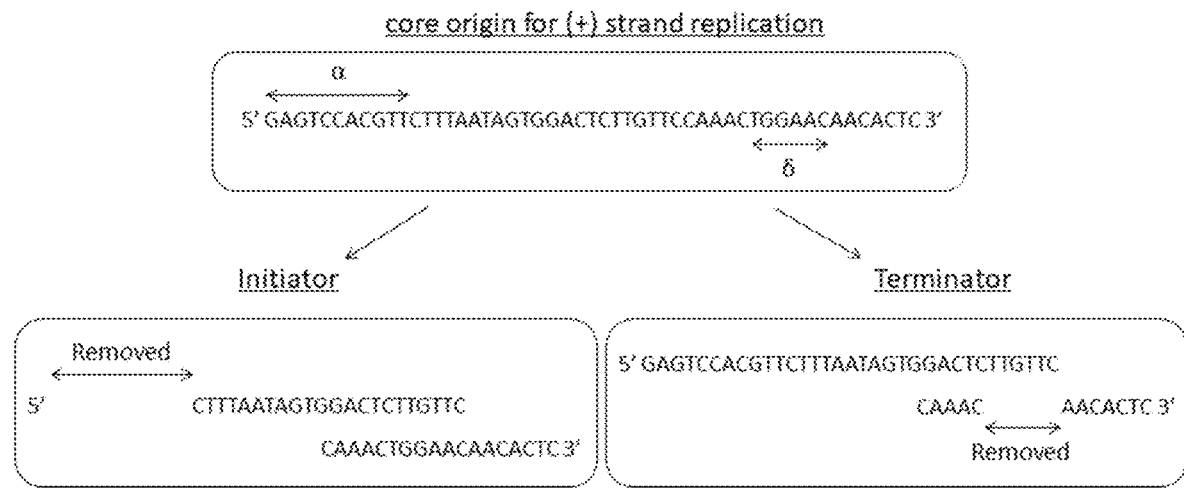
FIG. 2 shows DNA sequences of original and engineered M13 core origin for DNA replication. (Top box) The core origin works as an initiator as well as a terminator for (+) strand replication through a rolling circle mechanism. The α sequence is required for termination of DNA replication, while the δ sequence is essential to start DNA replication. (Left box) To eliminate the ability to complete DNA replication, the α sequence in the core origin was removed. This engineered initiator is used to initiate DNA replication. (Right box) The core origin without the δ sequence is used to stop DNA replication.

The Inho plasmid has been designed to ensure minimal extraneous base pair incorporation to the final phage ssDNA, thereby eliminating undesired ssDNA byproducts. For filamentous M13 phage replication, single-stranded phage DNA enters the cytoplasm upon infection and is converted into double-stranded replicative form (RF) by host enzymes. The phage replication proteins (P2) bind to the (+) strand origin, and nicking occurs at a specific single-stranded site. The replication of (+) strand is initiated at a nicking site in a rolling circle fashion and terminated at the same site by cleaving and circularizing the replicated ssDNA. Thus, the core origin sequences for (+) strand synthesis in FIG. 2 (top box) have roles for both initiation and termination of ssDNA replication.

In systems described herein, the core f1-ori for (+) strand replication was genetically engineered to separate its functions in order to develop a distinct initiator and terminator. It was previously reported that the α sequence is only required for termination of replication (Dotto et al., PNAS, 1982). The sequence from the core origin was knocked out to remove its ability to terminate DNA replication, which resulted in an engineered f1-ori sequence that functions only as an initiator (FIG. 2 (left box)). To make a terminator, one of the P2 binding sites of the core origin was disturbed. When one of P2 binding site was eliminated, the 'δ' sequence, from the f1-ori, the engineered f1-ori sequences are not able to initiate the replication of (+) strand synthesis. As a result, the engineered f1-ori without the δ sequence works as a f1-ori terminator (FIG. 2 (right box)).

Example 3: Production of Engineered Phages Having ssDNA of a Uniform Length

Figure 3A:
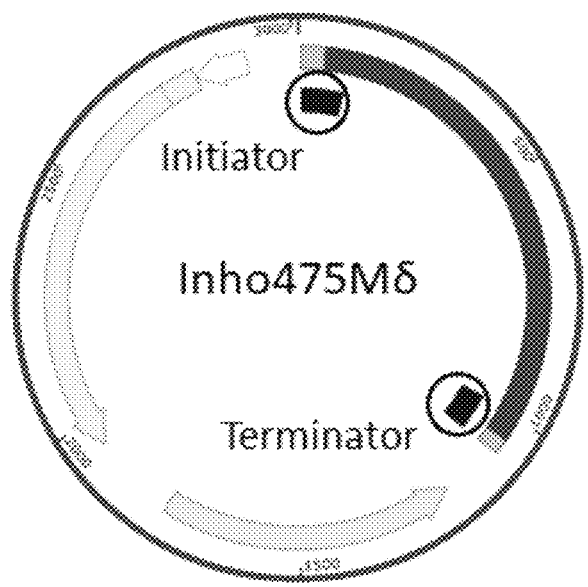
FIG. 3A shows an Inho plasmid map for production of engineered phage having 475 bp ssDNA. The Inho plasmid is constructed such that 475 bp are inserted between the engineered initiator and engineered terminator.
Figure 3B:
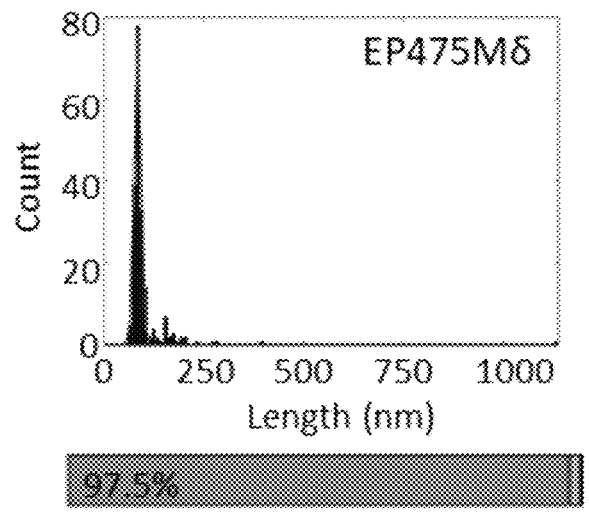
FIG. 3B shows a graph of size distribution of engineered phage having 475 bp ssDNA produced in accordance with some embodiments of the technology described herein.
Figure 3C:
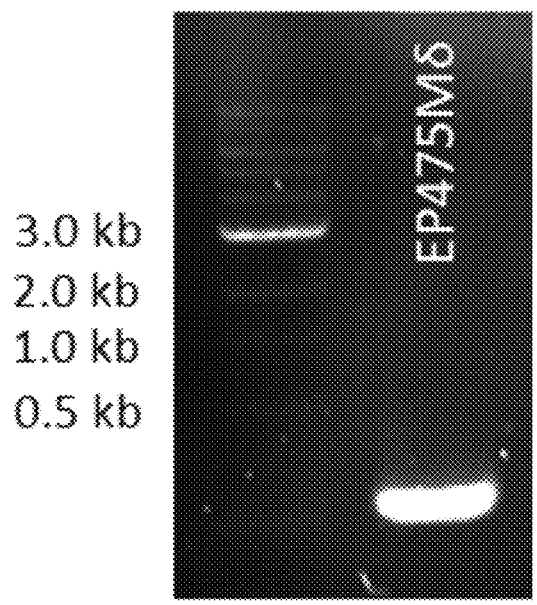
FIG. 3C shows a picture of an agarose gel from gel electrophoresis of ssDNA extracted from engineered phage having 475 bp ssDNA produced in accordance with some embodiments of the technology described herein.

The initiator and the terminator f1-ori sequences were positioned in the Inho phagemid, and the DNA sequences between the initiator and the terminator (indicated by the double-sided arrow outside of Inho plasmid in FIG. 1) are produced in the host cells. As shown in FIG. 3A, the Inho475Mδ phagemid having 475 bases between the f1-ori initiator and the terminator was constructed. The Inho475Mδ phagemid co-transformed with M13-f1 plasmid produced engineered phage having 475 bp of ssDNA (EP475Mδ). The size distribution of EP475Mδ was measured using TEM. The cultured engineered phage shows ~97.5% uniform length of 95.0±3.2 nm (FIG. 3B). Dnase I was applied to the purified engineered phage solution to remove any unwanted, external DNA strands. After inactivation and removal of Dnase I from the solution, circular ssDNA from EP475Mδ was isolated as described herein. The extracted ssDNA showed a significant single band by gel electrophoresis (FIG. 3C).

Figure 4A:
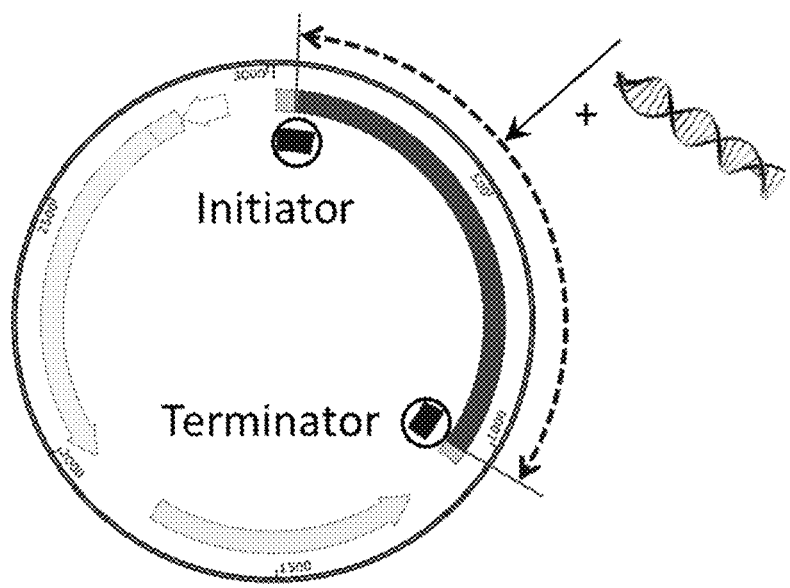
FIG. 4A shows an Inho plasmid map illustrating that the size of engineered phage is controlled by deleting or inserting DNA sequences of arbitrary sizes between the engineered initiator and the engineered terminator.
Figure 4B:
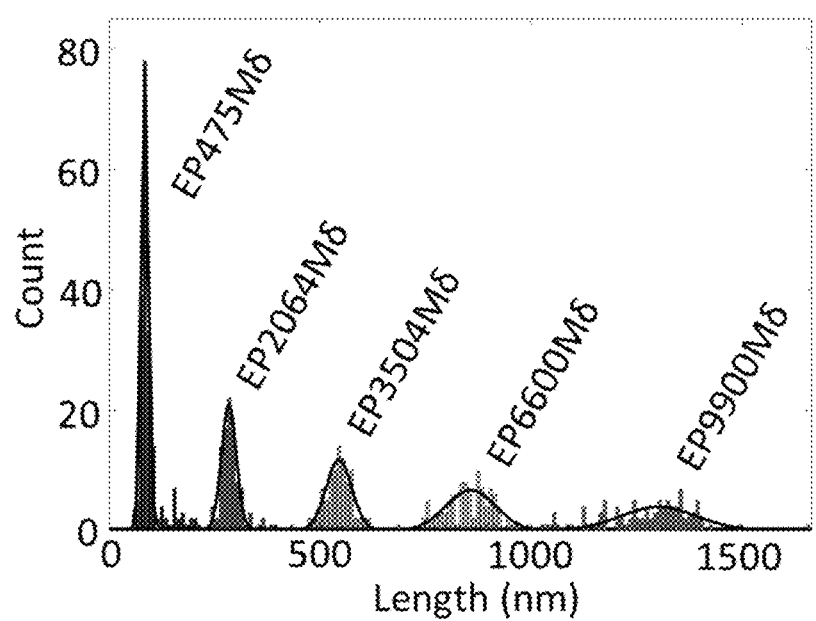
FIG. 4B shows a graph of size distribution of engineered phage having 475, 2064, 3504, 6600, and 9900 bp ssDNA produced in accordance with some embodiments of the technology described herein.
Figure 4C:
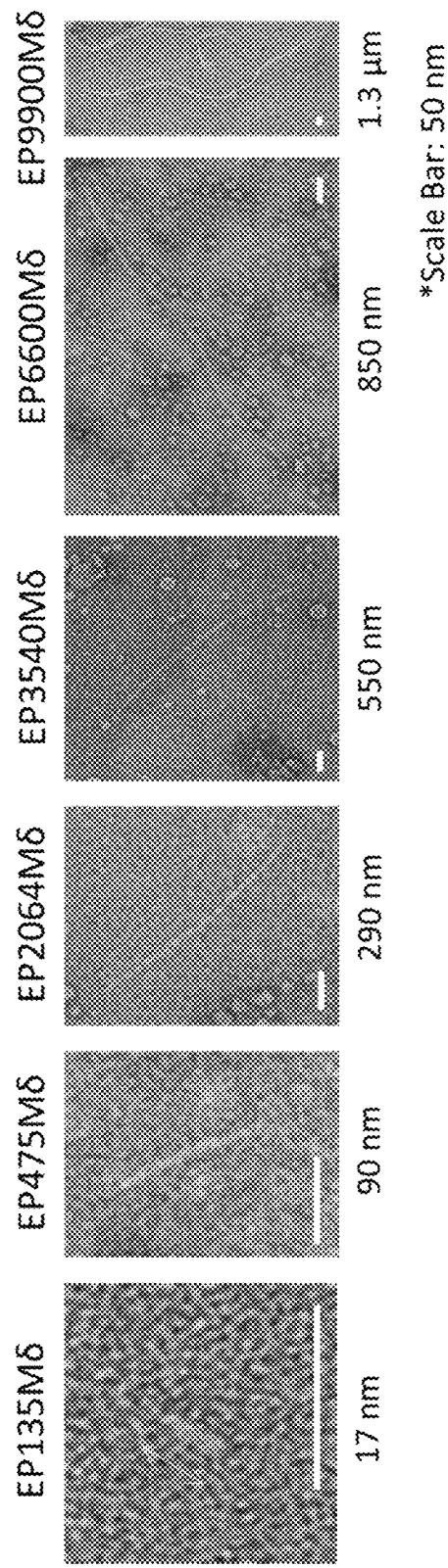
FIG. 4C shows TEM images of engineered phage having 475, 2064, 3504, 6600, and 9900 bp ssDNA produced in accordance with some embodiments of the technology described herein. Scale bar is 50 nm.

Arbitrary DNA strands were added into the region between the f1-ori initiator and terminator in Inho475Mδ phagemid to control length of engineered phage and to produce different lengths of ssDNA (FIG. 4A). The following were constructed by adding arbitrary DNA sequences: Inho2064Mδ, Inho3504Mδ, Inho6600Mδ, and Inho9900Mδ. The engineered Inho phagemid co-transformed with the M13-f1 plasmid produced EP2064Mδ, EP3504Mδ, EP6600Mδ, and EP9900Mδ that showed uniform size distribution (FIG. 4B). The average sizes of EP2064Mδ, EP3504Mδ, EP6600Mδ, and EP6600Mδ were 288.3±4.2, 567.4±22.8, 852.2±9.0, 1272.7±18.0 nm, respectively. Additionally, DNA sequences from Inho475Mδ were deleted to construct Inho135Mδ, which produced an engineered phage of ~20 nm. Representative TEM images of engineered phage having different lengths are shown in FIG. 4C. These results verified production of any length of engineered phage and circular ssDNA strands using systems, methods, and compositions provided herein.

Figure 5:
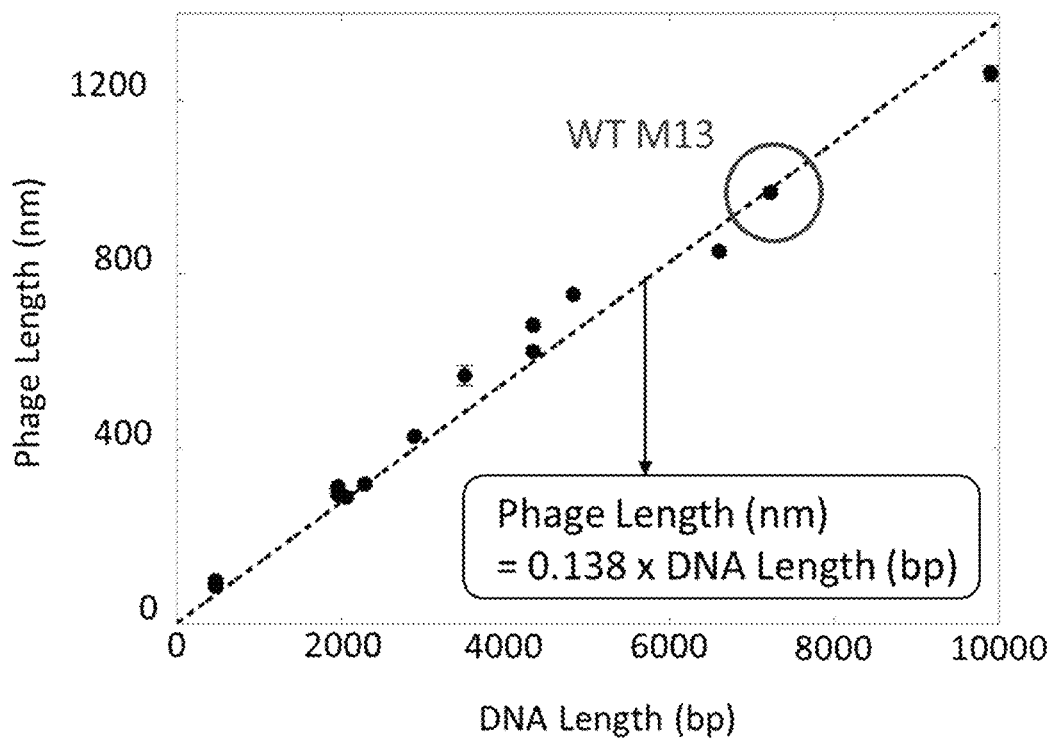
FIG. 5 shows a graph of engineered phage length (nm) plotted against DNA length (bp). The size of the phage is linearly proportional to the DNA length. The circle indicates wild-type M13 phage.

Inho phagemids for different sizes of engineered phages were constructed by adding or deleting DNA strands between f1-ori initiator and terminator, and phage length distribution was measured. The lengths of engineered phage and ssDNA genome were plotted, which demonstrated that the sizes of engineered phage are linearly proportional to lengths of ssDNA genome (FIG. 5).

Taken together, these results demonstrate that systems, methods, and compositions described herein may be used to produce any length of engineered phage having any length of circular ssDNA.

REFERENCES

Chen, F. Q. et al. High-frequency genome editing using ssDNA oligonucleotides with zinc-finger nucleases. *Nature Methods* 8, 753-755, doi:10.1038/nmeth.1653 (2011).

Cong, L. et al. Multiplex Genome Engineering Using CRISPR/Cas Systems. *Science* 339, 819-823, doi:10.1126/science.1231143 (2013).

Xiong, A. S. et al. PCR-based accurate synthesis of long DNA sequences. *Nature Protocols* 1, 791-797, doi:10.1038/nprot.2006.103 (2006).

Kosuri, S. & Church, G. M. Large-scale de novo DNA synthesis: technologies and applications. *Nature Methods* 11, 499-507, doi:10.1038/nmeth.2918 (2014).

Rothemund, P. W. K. Folding DNA to create nanoscale shapes and patterns. *Nature* 440, 297-302, doi:10.1038/nature04586 (2006).

Han, D. R. et al. Single-stranded DNA and RNA origami. *Science* 358, eaao2648, doi:10.1126/science.aao2648 (2017).

Keefe, A. D., Pal, S. & Ellington, A. Aptamers as therapeutics. *Nature Reviews Drug Discovery* 9, 537-550, doi:10.1038/nrd3141 (2010).

Merrifield, R. B. Solid phase peptide synthesis. 1. Synthesis of a tetrapeptide. *Journal of the American Chemical Society* 85, 2149-2154, doi:10.1021/ja00897a025 (1963).

Gyllensten, U. B. & Erlich, H. A. Generation of single-stranded-dna by the polymerase chain-reaction and its application to direct sequencing of the HLA-DQA locus. *Proceedings of the National Academy of Sciences of the United States of America* 85, 7652-7656, doi:10.1073/pnas.85.20.7652 (1988).

Hultman, T., Stahl, S., Homes, E. & Uhlen, M. Direct solid-phase sequencing of genomic and plasmid dna using magnetic beads as solid support. *Nucleic Acids Research* 17, 4937-4946, doi:10.1093/nar/17.13.4937 (1989).

Walder, R. Y., Hayes, J. R. & Walder, J. A. Use of PCR primers containing a 3'-terminal ribose residue to prevent cross-contamination of amplified sequences. *Nucleic Acids Research* 21, 4339-4343, doi:10.1093/nar/21.18.4339 (1993).

Ducani, C., Kaul, C., Moche, M., Shih, W. M. & Hogberg, B. Enzymatic production of 'monoclonal stoichiometric' single-stranded DNA oligonucleotides. *Nature Methods* 10, 647-652, doi:10.1038/nmeth.2503 (2013).

Dotto, G. P., Horiuchi, K. & Zinder, N. D. Initiation and termination of phage f1 plus-strand synthesis. *Proceedings of the National Academy of Sciences of the United States of America—Biological Sciences* 79, 7122-7126, doi:10.1073/pnas.79.23.7122 (1982).

What is claimed:

1. A method for producing single-stranded DNA (ssDNA) having uniform length, the method comprising:
providing a host cell comprising an engineered nucleic acid comprising an engineered initiator sequence and an engineered terminator sequence from a filamentous bacteriophage; and a DNA sequence of interest, wherein the DNA sequence of interest is located 3' to the engineered initiator sequence and 5' to the engineered terminator sequence; and a nucleic acid helper plasmid for expressing a plurality of bacteriophage proteins capable of assembling a single-stranded DNA (ssDNA) into a bacteriophage, wherein the engineered terminator sequence comprises the nucleic acid sequence of full length SEQ ID NO:1,
culturing the host cell under conditions suitable for producing a ssDNA from the DNA sequence of interest in the engineered nucleic acid and the plurality of bacteriophage proteins from the nucleic acid helper plasmid;
allowing the ssDNA and the plurality of bacteriophage proteins to assemble into an engineered phage; and
collecting the engineered phage and extracting the ssDNA from the engineered phage, wherein at least 90% of the extracted ssDNA is the same length as the DNA sequence of interest.

2. The method of claim 1, wherein at least 95% of the ssDNA is the same length as the DNA sequence of interest.

3. The method of claim 1, wherein the ssDNA is between 100 and 20,000 nucleotides in length.

4. The method of claim 1, wherein the ssDNA is circular.

5. The method of claim 1, further comprising the use of a selectable marker.

6. The method of claim 1, wherein the host cell is a bacterial cell.

7. The method of claim 6, wherein the bacterial cell is an *E. coli* cell.

8. The method of claim 1, wherein the plurality of bacteriophage proteins comprises P1, P2, P3, P4, P5, P6, P7, P8, P9, P10, and P11.

* * * * *

SEQUENCE LISTING

```
<160> NUMBER OF SEQ ID NOS: 3

<210> SEQ ID NO 1
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 1
gagtccacgt tctttaatag tggactcttg ttccaaactg gaacaacact c          51

<210> SEQ ID NO 2
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 2
ctttaatagt ggactcttgt tccaaactgg aacaacactc                        40

<210> SEQ ID NO 3
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 3
gagtccacgt tctttaatag tggactcttg ttccaaacaa cactc                  45
```